United States Patent [19]

Soeldner

[11] Patent Number: 4,855,242

[45] Date of Patent: Aug. 8, 1989

[54] METHOD OF DETECTING ANTIBODIES

[75] Inventor: J. Stuart Soeldner, Newton, Mass.

[73] Assignee: Joslin Diabetes Center, Inc., Boston, Mass.

[21] Appl. No.: 680

[22] Filed: Jan. 6, 1987

Related U.S. Application Data

[63] Continuation-in-part of Ser. No. 851,482, Apr. 14, 1986, abandoned.

[51] Int. Cl.$^4$ ........................................... G01N 33/539
[52] U.S. Cl. .................................. 436/539; 436/545; 436/804; 436/811; 435/7
[58] Field of Search ............... 436/539, 545, 804, 811; 435/7

[56] References Cited

U.S. PATENT DOCUMENTS 3,995,019  11/1976  Jerome .................................. 424/85

OTHER PUBLICATIONS

Kurtz et al., 18 Diabetologia 147 (1980).
Palmer et al., 222 Science 1337 (1983).
Salih et al., 41 Chem.-Biol. Interactions 169 (1982).
Miyamoto et al., 17 (1) Jap. J. Med. 15 (1978).
Osterman et al., 34 Steroids 575 (1979).
Henquin et al., 10 Diabetologia 61 (1974).
Ionescu-Tirgouiste et al., 27 Diab. 592 (1984).
Goldman et al., 27 Diab. 653 (1978).
Versijp et al., 15 Horm. Metabol. Res. 456 (1983).

Primary Examiner—Robert J. Warden
Assistant Examiner—Robert Benson

[57] ABSTRACT

A method for determining the quantity of an antibody in a sample, the method having the steps of: (1) providing a labelled antigen to the antibody; (2) contacting the labelled antigen with the sample in solution to form a labelled antigen-antibody complex; (3) providing an agent for precipitating the complex; (4) mixing the solution containing the labelled antigen-antibody complex with the precipitating agent to produce a precipitate and a supernatant; the supernatant containing labelled antigen and the precipitate containing the labelled antigen-antibody complex and uncomplexed labelled antigen; and (5) measuring the quantity of label in the precipitate or the supernatant in a manner substantially independent of the amount of uncomplexed labelled antigen in the precipitate.

29 Claims, 2 Drawing Sheets

METHOD OF DETECTING ANTIBODIES

This application is a continuation-in-part of Soeldner U.S. Ser. No. 851,482, filed Apr. 14, 1986, now abandoned.

BACKGROUND OF THE INVENTION

This invention relates to assays for antibodies.

Kurtz et al., 18 Diabetologia 147 (1980), describes a radioassay for insulin and proinsulin antibodies in serum. Serum is contacted with $^{125}$I-labelled ligand (insulin or proinsulin) having "approximately 200,000 cpm/ml"; the resultant solution is incubated for 24 hours; bound ligand is precipitated with 15% polyethylene glycol; the precipitate is washed once with 12.5% polyethylene glycol; and the amount of label in the precipitate is measured to obtain a qualitative measurement of antibody present in the serum.

Palmer et al., 222 Science 1337 (1983), describes using the radioassay of Kurtz et al. to measure the levels of insulin autoantibodies in persons clinically diagnosed as having insulin-dependent diabetes mellitus.

SUMMARY OF THE INVENTION

In general, the invention features a method for determining the quantity of an antibody in a sample, the method having the steps of: (1) providing a labelled antigen to the antibody; (2) contacting the labelled antigen with the sample in solution to form a labelled antigen-antibody complex; (3) providing an agent for precipitating the complex; (4) mixing the solution containing the labelled antigen-antibody complex with the precipitating agent to produce a precipitate and a supernatant, the supernatant containing labelled antigen and the precipitate containing the labelled antigen-antibody complex possibly contaminating uncomplexed labelled antigen; and (5) measuring the quantity of label in the precipitate or the supernatant in a manner substantially independent of the amount of any contaminating uncomplexed labelled antigen in the precipitate.

In preferred embodiments, step (5) includes the steps of: (a) measuring the quantity of the label in the precipitate; (b) determining the quantity of the label in the precipitate not attributable to the labelled antigen-antibody complex; and (c) determining the quantity of the antibody in the sample by subtracting the result of step (b) from the result of step (a). In step (b), the quantity of the uncomplexed labelled antigen present in the precipitate is determined by (i) providing a control sample that is identical to the sample; (ii) providing an unlabelled antigen to the antibody; (iii) contacting the control sample in solution with the unlabelled antigen to form an unlabelled antigen-antibody complex; (iv) contacting the solution containing the unlabelled antigen-antibody complex with the labelled antigen to the antibody, the quantity of the labelled antigen added being the same as the quantity added in step (2); (v) mixing the solution containing the unlabelled antigen-antibody complex with the same quantity of the precipitating agent used in step (4) to cause a precipitate to form, the precipitate containing the unlabelled antigen-antibody complex, possibly contaminating unlabelled antigen, and possibly contaminating labelled antigen, the labelled antigen being present in the same quantity as in the precipitate formed in step (4); and (vi) providing a measurement of the quantity of label in the precipitate; wherein the quantity of the unlabelled antigen contacted with the control sample in step (iii) is sufficient to preclude substantially all said labelled antigen contacted in step (iv) from forming a labelled antigen-antibody complex.

In other preferred embodiments, step (5) includes the steps of: (a) providing a control sample that is identical to the sample; (b) providing an unlabelled antigen to the antibody; (c) contacting the control sample in solution with the unlabelled antigen to form an unlabelled antigen-antibody complex; (d) contacting the solution containing the unlabelled antigen-antibody complex with labelled antigen to the antibody, the quantity of the labelled antigen added being the same as the quantity added in step (2); (e) mixing the solution containing the unlabelled antigen-antibody complex with the same quantity of the precipitating agent used in step (4) to produce a precipitate and a supernatant, the precipitate containing the unlabelled antigen-antibody complex, unlabelled antigen, and labelled antigen, the labelled antigen being present in the same quantity as in the precipitate formed in step (4); (f) providing a measurement of the quantity of the label in the supernatant produced in step (e); (g) providing a measurement of the quantity of the label in the supernatant produced in step (4); and (h) determining the quantity of the antibody in the precipitate by subtracting the result of step (g) from the result of step (f); wherein the quantity of the unlabelled antigen contacted with the control sample in step (iii) is sufficient to preclude substantially all the labelled antigen contacted in step (iv) from forming a labelled antigen-antibody complex.

In other preferred embodiments, the sample is serum; the antibody is islet cell autoantibody, proinsulin autoantibody, preproinsulin autoantibody, insulin A-chain autoantibody, insulin B-chain autoantibody, insulin C-peptide autoantibody, glucagon autoantibody, proglucagon autoantibody, preproglucagon autoantibody, somatostatin autoantibody, prosomatostatin autoantibody, preprosomatostatin autoantibody, pancreatic polypeptide hormone autoantibody, propancreatic polypeptide hormone autoantibody, and prepropancreatic polypeptide hormone autoantibody (pancreatic polypeptide hormone is a well-characterized hormone secreted by the pancreas, specifically by the islets of Langerhans). In a particular preferred embodiment the antibody is insulin autoantibody, the antigen is insulin, and the amount of the labelled insulin contacted with the serum in step (2) is between 2,000–35,000 nU of labelled insulin per milliliter of serum (nU=nanounit; 25 U=1 mg).

In another aspect the invention features a method for determining the quantity of antibody in a body fluid, the method having the steps of: (1) providing a controlled amount of labelled antigen to the antibody, the controlled amount not substantially exceeding the amount of natural antigen present in the body fluid; (2) contacting the labelled antigen with the body fluid to form a labelled antigen-antibody complex; (3) providing an agent for precipitating the complex; (4) mixing the solution containing the complex with the precipitating agent to produce a precipitate and a supernatant, the precipitate containing labelled antigen-antibody complex; and (5) measuring the quantity of label in the precipitate or the supernatant.

In preferred embodiments, the body fluid is serum; the antibody is insulin autoantibody; the antigen is insulin; and the amount of labelled insulin contacted with the serum is between 2,000–35,000 nanounits of labelled insulin per milliliter of serum.

In another aspect the invention features a method for determining the quantity of an antibody in a sample, the method having the steps of: (1) providing a labelled antigen to the antibody; (2) contacting the labelled antigen with the sample in solution to form a labelled antigen-antibody complex; (3) providing an agent for precipitating the complex; (4) mixing the solution containing the labelled antigen-antibody complex with the precipitating agent to produce a precipitate and a supernatant, the precipitate containing the labelled antigen-antibody complex and uncomplexed labelled antigen; (5) washing the precipitate at least twice with a washing agent to remove uncomplexed labelled antigen without dissolving labelled antigen-antibody complex, the supernatant from the first washing being combined with the supernatant produced in step (4); and (6) measuring the quantity of label in the precipitate or in the combined supernatants.

In preferred embodiments, the washing reduces the amount of labelled antigen in the precipitate to less than 5% of the total amount of label in the precipitate; the antibody is insulin autoantibody; the washing agent is 7–13% polyethylene glycol; the sample is serum; the antigen is insulin; and the amount of the labelled insulin contacted with the serum in step (2) is between 2,000–35,000 nanounits of labelled insulin per milliliter of serum.

In another aspect, the invention features a method for determining the quantity of an antibody in a body fluid, the method having the steps of: (1) providing a labelled antigen to the antibody; (2) contacting the labelled antigen with the body fluid and incubating the resultant solution for a period sufficient to allow substantially all naturally present antigen to dissociate from the antibody and to form a labelled antigen-antibody complex; (3) providing an agent for precipitating the complex; (4) mixing the solution containing the labelled antigen-antibody complex with the precipitating agent to produce a precipitate and a supernatant, the supernatant containing uncomplexed labelled antigen and the precipitate containing the labelled antigen-antibody complex and uncomplexed labelled antigen; and (5) measuring the quantity of label in the precipitate or the supernatant.

In preferred embodiments, the body fluid is serum; the antibody is insulin autoantibody; the antigen is insulin; and the incubation period is at least seven days.

In another aspect the invention features a method of diagnosing insulin dependent diabetes mellitus in a person prior to the person being clinically diagnosed as having insulin dependent diabetes mellitus, the method having the steps of: (1) providing a serum sample of the person, the serum sample containing pancreatic hormone autoantibody (e.g., autoantibody to insulin or glucagon); (2) providing labelled pancreatic hormone (e.g., insulin or glucagon); (3) contacting the labelled pancreatic hormone with the serum to form a labelled hormone-hormone autoantibody complex; (4) providing an agent for precipitating the complex; (5) mixing the solution containing the complex with the precipitating agent to produce a precipitate and a supernatant, the precipitate containing the labelled complex; (6) measuring the quantity of label in the precipitate, the quantity indicating the quantity of the hormone autoantibody in the serum; (7) comparing the quantity of hormone autoantibody in the serum to a pre-determined threshold level; and (8) diagnosing the person as having insulin dependent diabetes mellitus if the quantity of the autoantibody in the serum is higher than the pre-determined threshold level.

The assays of the invention have greatly improved sensitivity and specificity, and can be used to detect both autoantibodies and antibodies produced in small amounts in response to exposure to antigens, e.g., non-human insulin.

Other features and advantages of the invention will be apparent from the following description of the preferred embodiments thereof, and from the claims.

DESCRIPTION OF THE PREFERRED EMBODIMENT

We turn now to the description of the preferred embodiment, after first briefly describing the drawings.

Drawings

REAGENTS AND BUFFERS $^{125}$I-labelled insulin was obtained from Cambridge Medical Diagnostics (catalogue number 130), Billerica, Mass.; bovine serum albumin from Fraction V-Arnel Products (catalogue number 3399), New York; bovine gamma globulin from Sigma Chemical Co. (catalogue number G-5009); Tween 20 from J.T. Baker Chemical Co. (catalogue number X251-7); and Humulin R U-100 from Eli Lilly Co., Indianapolis, Ind. The following reagents were obtained from Fisher Scientific Co.: sodium phosphate monobasic (catalogue number S-369); sodium phosphate dibasic (catalogue number S-374); sodium chloride (catalogue number S-271); barbital sodium C-IV (catalogue B-22); and carbowax PEG (polyethelylene glycol) 8000 (catalogue number P-156).

The composition of the buffers used in the assay are as follows (normal saline =0.9% NaCl solution):

0.04M Phosphosaline Protein Buffer
   16ml 0.2M sodium phosphate monobasic
   84ml 0.2M sodium phosphate dibasic
   0.125g bovine serum albumin
   0.063g bovine gamma globulin
   150ml normal saline 0.5M Veronal Buffer
   50ml of barbital stock solution
   (41.2g sodium barbital in one liter of distilled water)
   6ml 0.2M HCl
   144ml distilled water

Procedure

Figure 1:
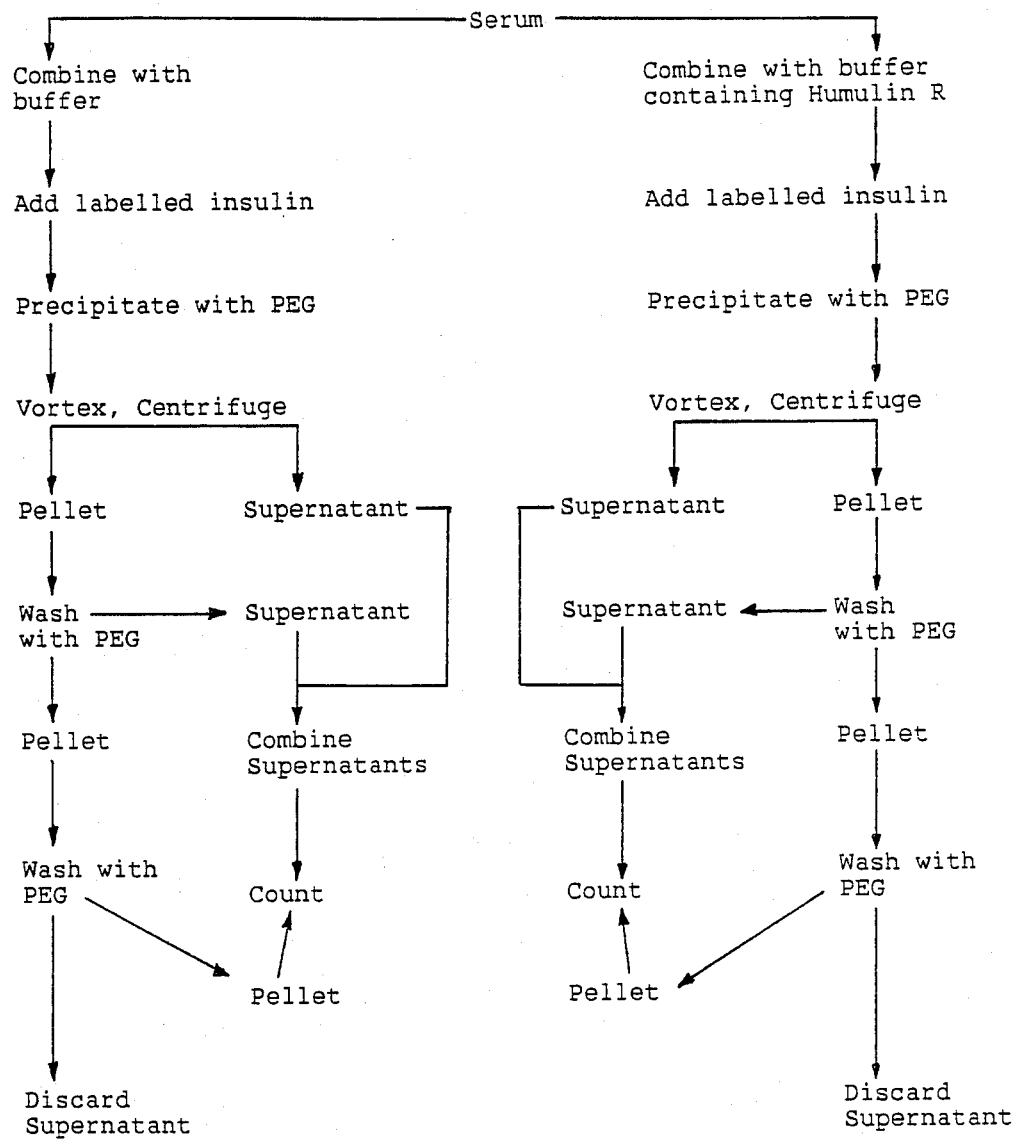
FIG. 1 is a flow diagram for a method of assaying insulin autoantibodies in serum.

There is shown in FIG. 1 a flow diagram for one method of assaying insulin autoantibodies in serum. 150 $\mu$l aliquots of serum, obtained from a person who has fasted overnight, are placed in four test tubes. Two of the aliquots are designated the test samples, and two are designated the control samples. 50 $\mu$l of 0.4M phosphosaline protein buffer (pH 7) are added to the test samples. 50 $\mu$l of the same buffer that additionally contains Humulin R (a form of insulin) at a concentration of 9,000,000 nU/ml are added to the control samples; the resulting control solutions contain 3,000,000 nU of Humulin R per ml of serum. All samples are incubated for at least 1 hour at 4° C.

$^{125}$I-labelled insulin is added to the test samples to form labelled insulin-insulin autoantibody complex. The amount of labelled insulin added should be within the range of insulin naturally present in the serum, which after an overnight fast is between 2,000–35,000 nanounits per milliliter of serum (5,000–15,000 nU/ml being the more common range and 10,000 nU/ml being the average). If less than that quantity is added, the amount of labelled insulin-insulin autoantibody complex formed may be insufficient to measure accurately, as the naturally present, unlabelled insulin may predominate as the insulin autoantibody binding partner. If more than that quantity is added, the signal associated with precipitated labelled insulin-insulin autoantibody (discussed below) may be drowned out by the signal associated with precipitated labelled uncomplexed insulin. For 150 µl of serum, 300–5250 nU (preferably 750–2250 nU, most preferably 1500 nU) of labelled insulin, diluted with phosphosaline protein buffer, are added.

The test samples are then incubated at least four days (preferably seven days; one day being 24 hours) at 4° C. An incubation period of shorter duration may be insufficient to allow for complete dissociation of naturally present unlabelled insulin that is tightly bound to insulin autoantibody, resulting in low readings of insulin autoantibody in the serum.

An identical amount of $^{125}$I-labelled insulin is added to the control samples. Only an insignificant amount of labelled insulin will bind to insulin autoantibody in the control samples because Humulin R, present in large excess (>99.5% of the total insulin) in these samples, has taken up substantially all the binding sites. The control samples are incubated at 4° C. for the same period of time as the test samples.

Following incubation, 1.5 ml of ice-cold 9–25% (preferably 12–15%, most preferably 14.3%) polyethylene glycol in 0.05M veronal buffer (pH 8.6) containing 0.1% Tween 20 is added to each sample to precipitate insulin-insulin autoantibody complex; 9–25% polyethylene glycol gives maximum precipitation of insulin-insulin autoantibody complex with minimum precipitation of uncomplexed insulin, although some of the latter will coprecipitate. The mixtures are vortexed and centrifuged, and the supernatants are decanted into clean tubes.

The precipitates, which are now in the form of pellets, are then washed at least twice (preferably 3 times) with a washing agent to dissolve uncomplexed $^{125}$I-labelled insulin to reduce the quantity of uncomplexed labelled insulin in the precipitate to less than 5% of the total amount of label in the precipitate (as measured in cpm). Each washing consists of adding to each pellet 1.5ml of between 7–13% (preferably 11% of ice-cold polyethylene glycol (a washing agent) in 0.05M veronal buffer (pH 8.6) containing 0.1% Tween 20, vortexing, and centrifuging; 7–13% polyethylene glycol dissolves the maximum amount of uncomplexed labelled insulin without dissolving significant amounts of insulin-insulin autoantibody complex. The supernatants from the first wash are added to the original supernatants; the supernatants from latter washes can be discarded.

At this point, the pellets derived from test samples contain $^{125}$I-labelled insulin-insulin autoantibody complex and some $^{125}$I-labelled uncomplexed insulin; the supernatants contain the remainder of the labelled uncomplexed insulin. The insulin-insulin autoantibody complex contained in the pellets derived from the control samples will be greater than 99.5% unlabelled because of the large excess of unlabelled insulin present during binding. The pellet, however, will contain approximately the same amount of $^{125}$I-labelled uncomplexed insulin as in the test sample pellets, with the remainder being dissolved in the control supernatants.

The pellets and supernatants are counted in a gamma counter for 9 minutes. Three empty assay tubes are also counted (in the middle of the run) to obtain a background count. Once the counting is completed, the percentage in the pellets of total $^{125}$I-labelled insulin is calculated by: (1) subtracting the background count from the recorded count for each pellet and supernatant; (2) dividing the supernatant counts by 0.55 in order to compensate for the 55% efficiency of the gamma counter with respect to these counts, caused by the large volume in the supernatant tubes; (3) totaling the counts for each pellet and associated supernatant; and (4) calculating the percentage of $^{125}$I-label in each pellet by dividing the pellet count by the combined pellet-supernatant count. The percentages of label in the test sample pellets are averaged, and the percentages of label in the control sample pellets are averaged.

To determine the percentage of total label in test sample pellets attributable to $^{125}$I-labelled insulin-insulin autoantibody complex, the average percentage of label in a control sample pellet—which is assignable to uncomplexed $^{125}$I-labelled insulin—is subtracted from the average percentage of label in a test sample pellet—which is assignable to uncomplexed $^{125}$I-labelled insulin and $^{125}$I-labelled insulin-insulin autoantibody complex.

The resulting percentage is easily converted into the concentration of insulin autoantibody in the serum. First, the fraction of labelled insulin that bound to insulin autoantibody is obtained by dividing the above percentage by 100. Second, by multiplying this fraction by the original concentration, with respect to serum, of labelled insulin (most preferably 10,000 nU/ml), the concentration of labelled insulin that reacted with insulin autoantibody, which is equal to the concentration of insulin autoantibody in serum, is obtained.

EXAMPLE

Figure 2:
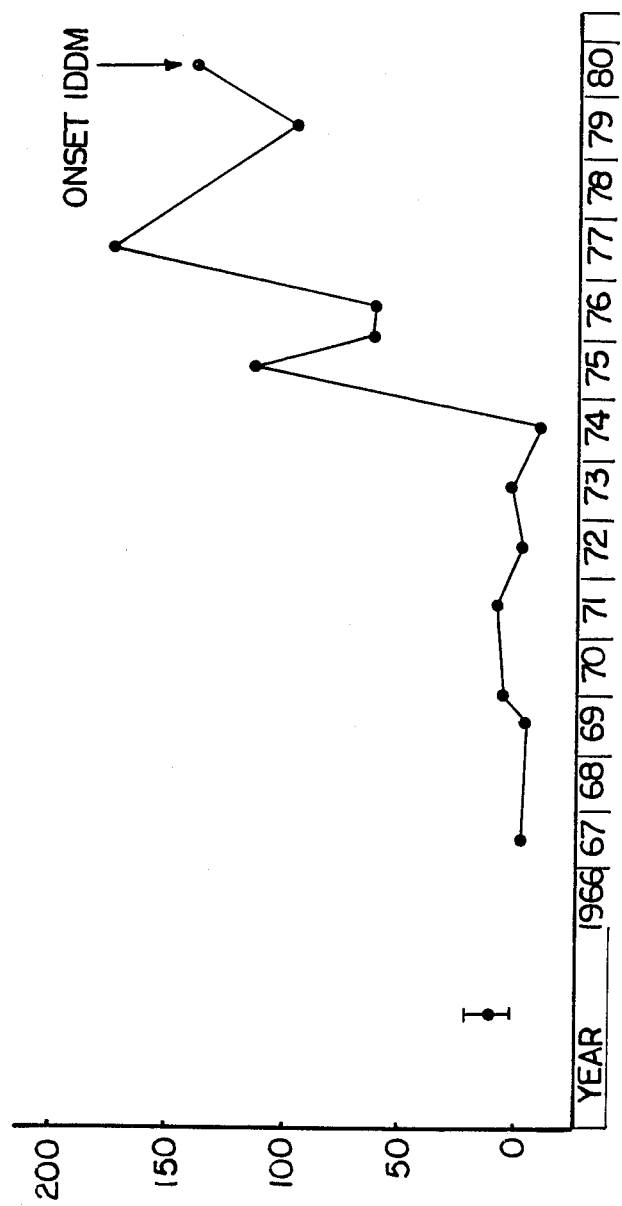
FIG. 2 shows the results of performing the assay of FIG. 1 on the serum of a person who was later clinically diagnosed as having insulin-dependent diabetes mellitus.

FIG. 2 shows the results of performing the above described assay on serum samples which had been collected periodically for a number of years prior to the person's being clinically diagnosed as having insulin dependent diabetes mellitus (IDDM). Clinical diagnosis normally occurs when polyuria, polydipsia, polyphagia, hyperglucemia, glycosuria, and acetonuria are manifested. The serum samples were tested in the above radioassay with one modification in procedure—following addition of $^{125}$I-labelled insulin, the samples were incubated for 2 days instead of 7 days.

The X axis in FIG. 2 is the year in which the serum sample was obtained and the Y axis is the level (in nU/ml of serum) of insulin autoantibodies detected in the serum. Normal levels of insulin autoantibodies in serum (11.2±9.8 nU/ml) are shown on the left side of the graph. The person had normal levels of insulin autoantibodies until approximately 5 years prior to being clinically diagnosed as having IDDM, at which point antibody levels increased dramatically and remained between approximately 55 and 165 nU/ml.

This example illustrates that IDDM can be detected prior to a clinical diagnosis of the disease by measuring the level of insulin autoantibodies present in serum. If the level of insulin autoantibodies is greater than a predetermined threshold level, IDDM is indicated. When a seven day incubation period is used in the procedure, the pre-determined threshold level is 31 nanounits of insulin autoantibodies per milliliter of serum.

Other Embodiments

Other embodiments are within the following claims. For example, other precipitating agents, such as either ammonium sulfate or hydrochloric acid in ethanol, can be used. Moreover, other antibodies can be detected by the methods of this invention. For example, antigenic determinants for islet cell autoantibodies can be isolated from islets of Langerhans, labelled, and then used to assay for islet cell autoantibodies in serum. Similarly, a labelled hormone secreted by the pancreas (those hormones, e.g., insulin and pancreatic polypeptide hormone, including prohormones and preprohormones, that are produced by pancreas cells) can be used to detect autoantibodies to the respective hormone. Thus, pre-proinsulin, insulin A-chain, insulin B-chain, C-peptide, glucagon, and proglucagon can be used to detect autoantibodies to, respectively, proinsulin, pre-proinsulin, insulin A-chain, insulin B-chain, C-peptide, glucagon, and proglucagon. Furthermore, labelled proinsulin may be used to detect the presence of insulin antibody. The assay can also employ, as the labelled hormone, human, non-human, synthetic, or natural hormone.

The assay was used to detect the level of glucagon antoantibody in serum. The same procedure used to detect the level of insulin antoantibody was used, with the exception that an equimolar amount of $^{125}$I-labelled glucagon was used in place of the labelled insulin, and an equimolar amount of unlabelled glucagon was used in place of unlabelled insulin.

IDDM can be detected prior to clinical diagnosis of the disease by measuring the level of other pancreatic hormone autoantibodies in the serum to hormones secreted by the pancreas. If the level of the pancreatic hormone autoantibodies is greater than a predetermined threshold level (the average upper concentration of the particular autoantibody that may be found in normal persons, i.e, those who are not beginning to develop IDDM), IDDM is indicated. For example, when assaying glucagon autoantibodies, the pre-determined threshold level is 100 fentograms of glucagon autoantibody per milliliter of serum.

The immunoassays of the invention may also be used to determine the level of insulin antibodies (or glucagon antibodies) in the serum of a person who has been receiving insulin injections (which often also include small quantities of glucagon).

The phosphosaline buffer used may contain higher concentrations of bovine serum albumin (e.g., 0.5%) and bovine gamma globulin (e.g., 0.5%).

What is claimed is:

1. A method for determining the quantity of an antibody in a sample, said method comprising the steps of
   (1) providing a labelled antigen to said antibody;
   (2) contacting said labelled antigen with said sample in solution to form a labelled antigen-antibody complex;
   (3) providing an agent for precipitating said complex;
   (4) mixing the solution containing said labelled antigen-antibody complex with said precipitating agent to produce a precipitate and a supernatant, said supernatant containing uncomplexed labelled antigen and said precipitate containing said labelled antigen-antibody complex and uncomplexed labelled antigen; and
   (5) measuring the quantity of label in said precipitate in a manner substantially independent of the amount of uncomplexed labelled antigen in said precipitate by
      (a) measuring the quantity of said label in said precipitate;
      (b) determining the quantity of said uncomplexed labelled antigen present in said precipitate by
         (i) providing a control sample that is identical to said sample,
         (ii) providing an unlabelled antigen to said antibody,
         (iii) contacting said control sample in solution with said unlabelled antigen to form an unlabelled antigen-antibody complex,
         (iv) contacting the solution containing said unlabelled antigen-antibody complex with said labelled antigen to said antibody, the quantity of said labelled antigen added being the same as the quantity added in step (2),
         (v) mixing said solution containing said unlabelled antigen-antibody complex with the same quantity of said precipitating agent used in step (4) to cause a precipitate to form, said precipitate containing said unlabelled antigen-antibody complex, said unlabelled antigen, and said labelled antigen, said labelled antigen being present in the same quantity as in said precipitate formed in step (4), and
         (vi) providing a measurement of the quantity of label in said precipitate; and
      (c) determining the quantity of said antibody in said sample by subtracting the result of step (b) from the result of step (a) and relating the difference in quantity of said label in said precipitates to the quantity of said antibody in said sample;
   wherein said quantity of said unlabelled antigen contacted with said control sample in step (iii) is sufficient to preclude substantially all said labelled antigen contacted in step (iv) from forming a labelled antigen-antibody complex.

2. The method of claim 1, wherein said quantity of said unlabelled antigen is at least ninety-eight times as great as said quantity of said labelled antigen.

3. The method of claim 1, wherein said sample is serum.

4. The method of claim 3, wherein said antibody is an autoantibody.

5. The method of claim 4, wherein said autoantibody is insulin autoantibody.

6. The method of claim 4, wherein said autoantibody is islet cell autoantibody.

7. The method of claim 4, wherein said autoantibody is proinsulin autoantibody.

8. The method of claim 4, wherein said autoantibody is preproinsulin autoantibody.

9. The method of claim 4, wherein said autoantibody is insulin A-chain autoantibody.

10. The method of claim 4, wherein said autoantibody is insulin B-chain autoantibody.

11. The method of claim 4, wherein said autoantibody is insulin C-peptide autoantibody.

12. The method of claim 4, wherein said autoantibody is glucagon autoantibody.

13. The method of claim 4, wherein said autoantibody is proglucagon autoantibody.

14. The method of claim 4, wherein said autoantibody is preproglucagon autoantibody.

15. The method of claim 4, wherein said autoantibody is somatostatin autoantibody.

16. The method of claim 4, wherein said autoantibody is prosomatostatin autoantibody.

17. The method of claim 4, wherein said autoantibody is preprosomatostatin autoantibody.

18. The method of claim 4, wherein said autoantibody is pancreatic polypeptide hormone autoantibody.

19. The method of claim 4, wherein said autoantibody is propancreatic polypeptide hormone autoantibody.

20. The method of claim 4, wherein said autoantibody is prepropancreatic polypeptide hormone autoantibody.

21. The method of claim 5, wherein said antigen is insulin.

22. The method of claim 21, wherein the amount of said labelled insulin contacted with said serum in step (2) is between 2,000–35,000 nanounits of labelled insulin per milliliter of said serum.

23. The method of claim 21, where the amount of said labelled insulin contacted with said serum in step (2) is between 5,000–15,000 nanounits of labelled insulin per milliliter of said serum.

24. The method of claim 1, wherein said precipitate formed in step (4) is washed at least twice with a washing agent to dissolve said uncomplexed labelled antigen without dissolving said labelled antigen-antibody complex, and said precipitate formed in step (5)(b)(v) is washed at least twice with a washing agent to dissolve said uncomplexed labelled antigen without dissolving said labelled antigen-antibody complex.

25. The method of claim 24, wherein said washing reduces the amount of said uncomplexed labelled antigen to less than 5% of the total amount of label in said precipitate.

26. The method of claim 5, wherein said precipitate formed in step (4) is washed at least twice with a washing agent to dissolve said uncomplexed labelled antigen without dissolving said labelled antigen-antibody complex, and said precipitate formed in step (5)(b)(v) is washed at least twice with a washing agent to dissolve said uncomplexed labelled antigen without dissolving said labelled antigen-antibody complex.

27. The method of claim 26, wherein said washing reduces the amount of said uncomplexed labelled antigen to less than 5% of the total amount of label in said precipitate.

28. The method of claim 27, wherein said washing agent is 7–13% polyethylene glycol.

29. A method for determining the quantity of an antibody in a sample, said method comprising the steps of (1) providing a labelled antigen to said antibody;
(2) contacting said labelled antigen with said sample in solution to form a labelled antigen-antibody complex;
(3) providing an agent for precipitating said complex;
(4) mixing the solution containing said labelled antigen-antibody complex with said precipitating agent to produce a precipitate and a supernatant, said supernatant containing uncomplexed labelled antigen and said precipitate containing said labelled antigen-antibody complex and uncomplexed labelled antigen; and
(5) measuring the quantity of label in said precipitate in a manner substantially independent of the amount of uncomplexed labelled antigen in said precipitate by
  (a) providing a control sample that is identical to said sample;
  (b) providing an unlabelled antigen to said antibody;
  (c) contacting said control sample in solution with said unlabelled antigen to form an unlabelled antigen-antibody complex;
  (d) contacting the solution containing said unlabelled antigen-antibody complex with said labelled antigen to said antibody, the quantity of said labelled antigen added being the same as the quantity added in step (2);
  (e) mixing said solution containing said unlabelled antigen-antibody complex with the same quantity of said precipitating agent used in step (4) to produce a precipitate and a supernatant, said precipitate containing said unlabelled antigen-antibody complex, said unlabelled antigen, and said labelled antigen, said labelled antigen being present in the same quantity as in said precipitate formed in step (4);
  (f) providing a measurement of the quantity of said label in said supernatant produced in step (e);
  (g) providing a measurement of the quantity of said label in said supernatant produced in step (4); and
  (h) determining the quantity of said antibody in said precipitate by subtracting the result of step (g) from the result of step (f) and relating the difference in quantity of said label in said supernatants to the quantity of said antibody in said sample;
  wherein said quantity of said unlabelled antigen contacted with said control sample in step (c) is sufficient to preclude substantially all said labelled antigen contacted in step (d) from forming a labelled antigen-antibody complex.

* * * * *